United States Patent [19]
Ermert et al.

[11] Patent Number: 6,155,981
[45] Date of Patent: Dec. 5, 2000

[54] DIAGNOSTIC ULTRASONIC IMAGING SYSTEM AND METHOD FOR DISCRIMINATING NON-LINEARITIES

[75] Inventors: Helmut Ermert, Roettenbach, Germany; John Lazenby, Fall City, Wash.; Martin Krueger, Bochum, Germany; Christopher Chapman, Redmond, Wash.; Wilko Wilkening, Bochum, Germany

[73] Assignee: Siemens Medical Systems, Inc., Iselin, N.J.

[21] Appl. No.: 09/200,257

[22] Filed: Nov. 25, 1998

Related U.S. Application Data

[60] Provisional application No. 60/066,612, Nov. 26, 1997.

[51] Int. Cl.⁷ ............................................. A61B 8/00
[52] U.S. Cl. ................................................... 600/453
[58] Field of Search .................... 600/443, 455, 600/454, 453, 456; 702/77

[56] References Cited

U.S. PATENT DOCUMENTS

| | | | |
|---|---|---|---|
| 5,177,691 | 1/1993 | Welles et al. | 702/77 |
| 5,357,964 | 10/1994 | Spivey et al. | 600/455 |
| 5,908,391 | 6/1999 | Muzillat et al. | 600/454 |

*Primary Examiner*—Marvin M. Lateef
*Assistant Examiner*—Maulin Patel

[57] ABSTRACT

In a diagnostic ultrasound imaging system, a sequence of more than two signals is transmitted into the interrogation of the patient's body. In one embodiment of the invention, the pulses are grouped as pairs that have an inverted phase, that is, one is time-domain negative of the other. In an alternative of this embodiment, the pulses need not be paired, but rather are generated with alternating phase characteristics. The return signals are then filtered to isolate (or suppress) return signal components corresponding to portions of the interrogation region with non-linear (or linear) response characteristics. In a second embodiment of the invention, three or more pulses are generated so that have non-equidistant relative phase distribution. By combining the return signals, linear return signal components are suppressed.

16 Claims, 2 Drawing Sheets

DIAGNOSTIC ULTRASONIC IMAGING SYSTEM AND METHOD FOR DISCRIMINATING NON-LINEARITIES

CROSS-REFERENCE TO RELATED APPLICATIONS

This application claims priority from U.S. Provisional Patent Application No. 60/066,612, filed Nov. 26, 1997.

BACKGROUND OF THE INVENTION

1. Field of the Invention

This invention involves a system and a method for imaging a portion of a human body using ultrasound.

2. Description of the Related Art

Viewed most generally, a diagnostic ultrasound imaging system works by transmitting a set of ultrasonic signals into a portion of a patient's body, sensing the resulting echo signals, and then interpreting the echo signals to form an image. A goal of all diagnostic ultrasonic imaging systems is to increase the clarity and resolution of the image so that more diagnostic information will be available to the physician. To this end, many different methods have been proposed for generating the transmission signal so that is has certain advantageous properties, for filtering the echo signals to eliminate certain unwanted components, or both.

One method that has recently shown great promise involves transmitting a pair of complex, amplitude-modulated ultrasonic pulses into the body in such a way that the second pulse is the time-domain "inverse" of the first. The second pulse, which is applied to the body as soon as possible after receiving the echo from the first transmitted pulse, can therefore be viewed, in one common representation of the two signals, as lying 180 degrees out of phase with the first pulse. The system then sums the time-domain return signals from each of the two transmitted pulses.

This technique is known variously as "pulse inversion," which accurately describes the relationship between the input pulses, "phase inversion," or even "harmonic imaging," since certain harmonics (usually the second) of the input signals are isolated. The advantage of this arrangement is that it isolates echo signals from body structures whose response is non-linear: Echo signals from body structures with a linear response will, by definition, in theory "cancel" each other upon summation, whereas echo signals from non-linear structures in general will not. U.S. Pat. No. 5,632,277 (Chapman, et al., issued May 27, 1997) for "Ultrasound Imaging System Employing Phase Inversion Subtraction to Enhance the Image;" and U.S. Pat. No. 5,706,819 (Hwang, et al., issued Jan. 13, 1998) for "Ultrasonic Diagnostic Imaging with Harmonic Contrast Agents" both describe such systems, although Hwang, et al., fail to realize that the pulse-inversion technique may be used to image tissue as well as micro-bubble contrast agents.

As always, what is needed is a system that discriminates between and images body structures even more clearly than what is now possible. This invention provides such a system.

SUMMARY OF THE INVENTION

The invention provides a system and method for generating and displaying an image of an interrogation region of a patient's body. The user of the system scans the interrogation region with an ultrasonic probe. The system transmits into the interrogation region with a pulse repetition frequency PRF a sequence of more than two pulses with alternating phase characteristics. The Doppler spectrum of return signals is then calculated from the sequence of transmitted pulses. The system then isolates in the Doppler spectrum components of the return signals corresponding to returns from portions of the interrogation region having non-linear response characteristics to the sequence of transmitted pulses. The thus isolated (filtered) image data is then displayed.

According to a second embodiment of the invention, the system generates and transmits a sequence of more than two pulses having non-equidistant relative phase characteristics. The return signals from the sequence of pulses are then combined, thereby isolating components of the return signals corresponding to returns from portions of the interrogation region having non-linear response characteristics to the sequence of transmitted pulses.

DETAILED DESCRIPTION

The system according to the invention is first described. Thereafter, various embodiments of the invention are explained, each involving a different manner either of generating ultrasonic pulses with certain relationships to each other, or of analyzing the return echo signals, or both.

System Description

Figure 1:
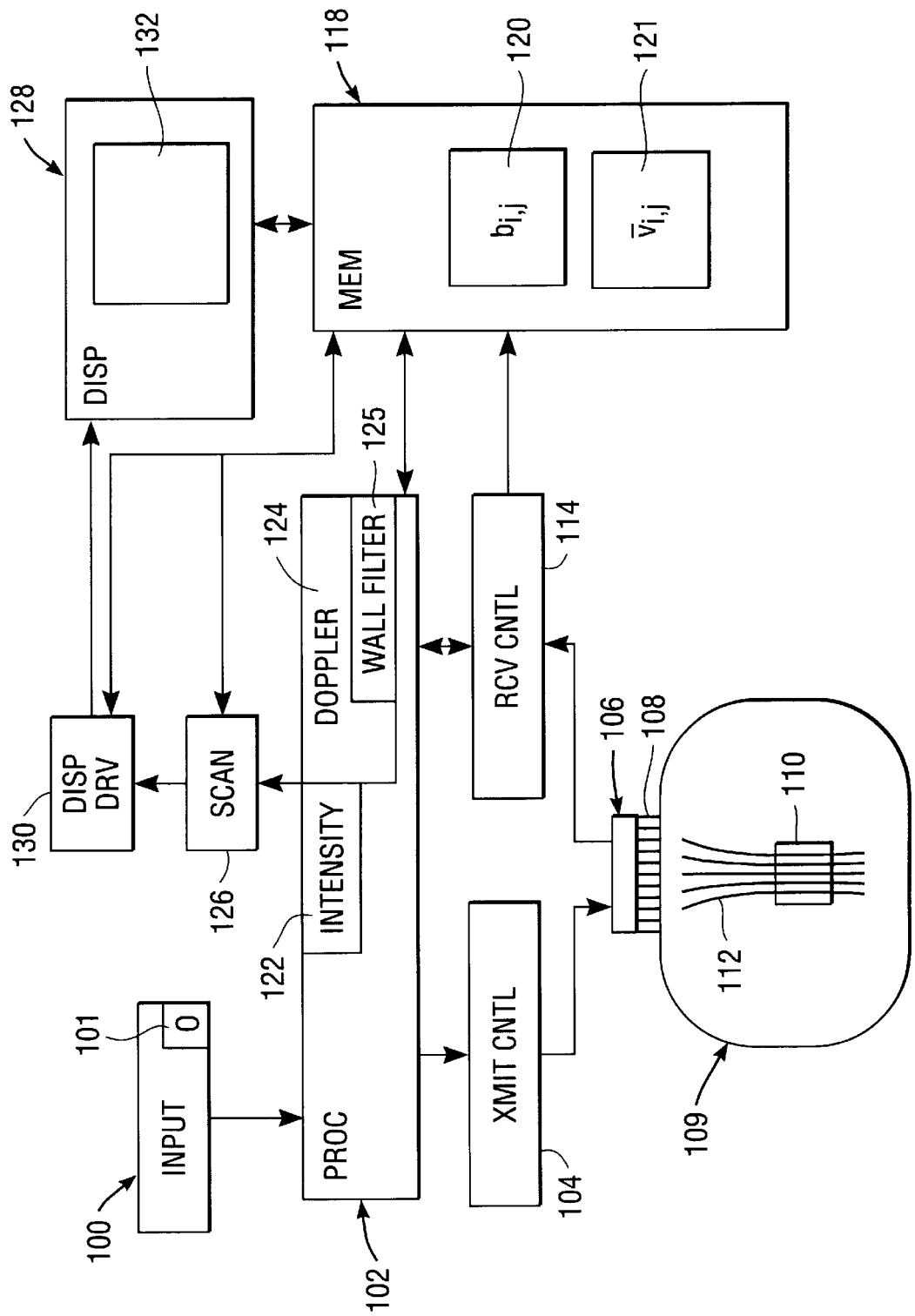
FIG. 1 is a block diagram showing the main components of an ultrasonic imaging system according to the invention.

FIG. 1 illustrates the main components of an ultrasonic imaging system according to the invention. The user enters various conventional scan parameters into an input unit 100, which typically includes such devices as a keyboard 101, knobs, and buttons. The input unit is connected to a processing system 102, which will typically be an electrically connected and cooperating group of processors such as microprocessors and digital signal processors; the processing system may, however, also be implemented by a single processor as long as it is fast enough to handle the various tasks described below.

As in known systems, the processing system 102 sets, adjusts, and monitors the operating parameters of a conventional transmission control circuit 104. This control circuit 104 generates and applies electrical control and driving signals to an ultrasonic probe 106, which includes an array piezoelectric elements 108. As is well known in the art, the piezoelectric elements generate ultrasonic waves when electrical signals of the proper frequency are applied to them.

By placing the probe 106 against the body 109 of a patient, these ultrasonic waves enter a portion 110 (an interrogation region) of the patient's body. By varying the phasing, amplitude, and timing of the driving signals in a conventional manner, the ultrasonic waves are focused to form a scan beam comprising a series of scan lines 112 that typically fan out from the probe.

In the most common applications of ultrasonic scanning, with linear arrays, the interrogation region 110 is scanned as a pattern of 2-D planes in order to generate 2-D image information, such as a spatial map of the intensity of echo signals returned from the interrogation region, or a 2-D map of the velocity of some tissue movement within the region. Other techniques using both one- and two-dimensional ultrasound arrays are, however, known that allow scan beams to lie in different planes and thus to generate 3-D representations of the scanned region, and to sense flow with three independent velocity components. The invention is able to operate with both 2-D and 3-D interrogation regions.

Ultrasonic echoes from the waves transmitted into the body return to the array 108 in the probe 106. In general, any body structure that has an acoustic impedance different from that of its surroundings will cause some echo. Such structures include body tissue, scatterers such as particles in the blood, bubbles in contrast agents, etc. Structures smaller than the wavelength of the ultrasonic signal may also return signals that are preferably not included in the displayed image. These echoes, commonly referred to as "speckle," represent one form of noise to be filtered out. Moreover, the portion of the body through which the ultrasound passes to image some reflector (such as scatterers, bubbles, tissue boundaries, etc.), may itself have non-linear sound propagation characteristics in addition to linear propagation characteristics. Any such structure or portion of the body that has a non-linear response component, either by scattering, reflection or propagation characteristics, is referred to in this discussion as a "non-linearity" or "non-linear structure."

As is well understood, the piezoelectric elements in the array convert the small mechanical vibrations caused by the echoes into corresponding radio-frequency (RF) electrical signals. Amplification and other conventional signal conditioning is then applied to the return signals by a reception controller 114. This processing includes, as needed, such known signal conditioning as time-gating, gain compensation, and diffraction compensation, in order to identify the echo signals that correspond to each scan plane of the interrogation volume 110. The type of conventional signal processing needed will in general depend on the particular implementation of the invention and can be chosen using known design methods.

The reception controller 114, all or part of which is normally integrated into the processing system 102 itself, converts the ultrasonic, radio-frequency (RF) return signals (typically on the order of a few to tens of megahertz) into lower frequency ranges for processing, and may also include analog-to-digital conversion circuitry. This is well known in the art of ultrasonic imaging.

In systems that generate a representation of the interrogation region as a discretized pattern of brightness or signal intensity values $b_{i,j}$, ($b_{i,j,k}$ for 3-D imaging) the downconverted power values for the two-dimensional interrogation region are stored in a memory 118 as image frame data 120, after conventional beamforming. An intensity-determining portion 122 of the processing system 102 may be included to perform the conventional calculations necessary for relating returned echo signal strengths to a predetermined range of intensity values.

The Doppler shifts and/or the power Doppler spectra for the various echo signals may also be determined, with necessary conventional calculations being performed in a Doppler/velocity-determining portion 124 of the processing system 102. Using the Doppler data and any known technique, the Doppler/velocity-determining portion 124 calculates a velocity vector $\bar{v}_{i,j}$ (or other conventional Doppler data, such as Doppler shift data), for each position (i,j) (for the 2-D case) in the discretized pattern representing the scanned interrogation region. In order to implement the first embodiment of the invention described below, the Doppler processing portion 124 includes a wall filter 125, whose characteristics are also described below.

Each frame of the image is represented and stored digitally as an array of acoustic power or intensity values $b_{i,j}$ and/or velocity vectors $\bar{v}_{i,j}$. These values $b_{i,j}$ and $\bar{v}_{i,j}$ are stored in respective memory portions 120, 121. Each set of frame data corresponds to one image frame, that is, to a 2-D cross section or 3-D sub-volume of the interrogation volume.

The interrogation region is normally not in the same shape as what the user wants to see displayed, and even when it is, the digital acoustic intensity values that make up the frame data are normally not in a form suitable for driving a conventional gray-tone or color display directly. The acoustic intensity or velocity values for an image frame are therefore applied to a conventional scan converter 126, which converts the digital acoustic values into display intensity values that are suitable for use in driving a display device 128.

The display device 128 typically includes or is connected to a conventional display driver 130 and includes a screen 132 (for example, LED or CRT) that is divided into an X-Y (or polar) matrix or pattern of picture elements or "pixels" that make up an image that the user can view and interpret. Note that a displayed image element will often be made up of more than one pixel, but that this will depend on the relative resolutions of the scan and of the display. The invention does not require any particular relative resolution.

Multi-Pulse Transmits

This invention provides several alternatives to the simple phase-inversion method found in the prior art, which is described above. The alternatives include transmitting a series of mutually phase-inverted pairs; transmitting a sequence of more than two pulses that alternate in phase by 180 degrees; and generating and transmitting sets of three or more pulses with both equidistant and non-equidistant phase distribution. These techniques are described individually below.

Sequenced Transmits With 180-Degree Relative Phase Shift

According to one aspect of the present invention, a sequence of pulse pairs [P11(t), P12(t)], [P21(t), P22(t)], ..., [Pn1(t), Pn2(t)] is generated (under control of the transmit controller 104) and applied to the patient's body. In each pair, the second pulse is generated "inverted" relative to the first, that is, Pm1(t)=−Pm2(t), m∈1, ..., n, where time is measured from the beginning of transmission of each respective pulse. This inversion can be considered "phase inversion," "pulse inversion," or even "polarity inversion," depending on how one chooses to define and analyze the relationship between the signals. As an alternative, the pulses need not be transmitted as pairs (one following immediately after the other, separated from the next pair by a greater time), but rather are transmitted at a constant rate but with alternating polarities; in other words, each pulse is inverted relative to the one transmitted before and after it. One advantage of both of these methods is that they improve the signal-to-noise ratio. Experiments with actual data from non-linear reflectors have, however, revealed, further advantages.

According to this first embodiment of the invention, the system collects and stores the return echo data from each pulse. The data (corresponding to intensity values) returned from each pulse correspond to what is conventionally referred to as an "A-line," which can be viewed as a vector. The collection of all vectors fired (transmitted) along the same beam line therefore forms an "ensemble." The collection of ensemble data (albeit not from the related, phased transmit pulses according to the invention) is a well-known technique in conventional Doppler processing in diagnostic ultrasound systems.

Echoes from sequences of multiple transmits with 180-degree relative phase shift can be processed using conventional Doppler processing, including Color Doppler and Power Doppler processing. In particular, wall filters such as wall filter 125 may be used to select for analysis and display different types of nonlinear-specific signals.

To understand this, consider that, in conventional Doppler imaging, signals returned from all stationary structures appear at DC in the Doppler spectrum. If the transmit signals have alternating 180-degree phase shifts, however, then signals returned from stationary linear structures appear at the frequency PRF/2. Signals returned from stationary non-linear structures have a component at DC. Signals returned from moving linear structures appear at Doppler shifts away from (both higher and lower) PRF/2. Signals returned from moving non-linear structures appear at Doppler shifts away from DC. The wall filter 125 may therefore select which of the four types of structures are to be isolated, analyzed, and displayed. The wall filter 125 should have the following characteristics in order to select each of the four types of structures:

| Structure Type | Wall Filter Characteristics |
|---|---|
| Stationary, linear | Single pass-band centered at PRF/2 |
| Moving, linear | Pass band on either side of PRF/2 (double pass-band) |
| Stationary, non-linear | Single pass-band centered at DC |
| Moving, non-linear | Pass band on either side of DC (double pass-band) |

The wall filter 125 may be designed using any known technique so that it has the desired characteristics. The design of such digital band-pass filters is well known, and will depend on the particular implementation. For example, the PRF in any given implementation will obviously affect the filter coefficients. What is new, however, is that the information selected or passed by the filter indicates the presence and spectral characteristics of non-linear (or linear, depending on how the filter is implemented) structures.

The specificity of this technique is limited by the fact that, for sufficiently high velocities, the Doppler shift may be comparable to PRF/2 and cause overlapping or "aliasing." In that case, this technique will no longer correctly discriminate linear and non-linear structures.

In a two- or multi-pulse transmit system, it is difficult to distinguish scatterers (or other reflectors) with strong scattering strength but weak linearity from those with weak scattering strength but strong linearity. According to the invention, the system distinguishes between these two cases by calculating (in the processor) the ratio of the power in the combined receive signal to the total power in all of the received signals. In the absence of noise and motion, this ratio—the non-linearity ratio—will indicate the degree of non-linearity of the scatterers with the scattering strength normalized out.

In most actual ultrasound systems, there is a small amount of intrinsic non-linearity, which makes all scatterers appear slightly non-linear to the system. The non-linearity ratio may then be used, by comparing it with an experimentally or theoretically determined threshold, to eliminate this effect.

One of the difficulties in all systems that use multiple, related pulses is that they are sensitive to changes in the received signal from one transmit to the next. The predominant causes of these unwanted changes are motion and noise. The effects of the noise can be reduced using any of the of the great number of methods currently available in ultrasonic imaging systems.

Even in two-pulse systems in the prior art, such as those described in U.S. Pat. Nos. 5,632,277 and 5,706,819, there is an assumption that reflectors do not move significantly between pulses. It can be shown, for example, that a change of reflector location of only 1 $\mu$m, with a carrier or transmit frequency of 4 MHz causes a phase error (deviation from the assumed 180 degrees) of from one to two degrees. This in turn leads to an approximately 1% reduction in the ability of the system to suppress echoes from linear reflectors.

Conventional systems attempt to reduce the effect of reflector motion by transmitting the second pulse in a pair as close in time as possible to the first pulse, thereby leaving less time for reflectors to move. This solution is, however, limited by the requirement that the second pulse cannot be transmitted until the echoes from the first pulse are received, at least not without sacrificing resolution.

This conventional solution (rapid transmission of pulse pairs and sequences) is preferably also used in this invention. In order to reduce the effects of motion even further, however, the invention preferably also includes at least one wall filter that remove motion signals at least for low velocities, while still allowing the non-linear signal components to pass. Conventional techniques may be used to design and apply such a wall filter to the echo data.

Transmit Pulses with Multiple Phase Shifts

Conventional two-pulse "phase inversion" imaging uses a train of two transmit pulses $s_1$, $s_2$ where the second pulse is the negative of the first pulse:

$$s_1(t)=s_0(t) \quad s_2(t)=-s_0(t)$$

$$s(t)=s_1(t)+s_2(t-T_{PRF})$$

where $s_0(t)$: transmit pulse used in B-mode $s(t)$: train of pulses $s_1$ and $s_2$ $T_{PRF}$: delay between $s_1$ and $s_2$, corresponding to the reciprocal of the Pulse Repetition Frequency (PRF) in PW-Doppler imaging.

Adding the receive signals $e_1$ and $e_2$, where $e_1$ and $e_2$ are the echoes (which can be separated conventional by time-gating) corresponding to transmit pulse $s_1$ and $s_2$, one gets:

$$e(t)=e_1(t-T_{PRF})+e_2(t)$$

which has a result of zero in case of linear propagation, scattering, and reflection:

$$e_n(t)=h(t)*s_n(t)$$

$$e(t)=h(t)*[s_0(t)-s_0(t)]=0$$

In case of a non-linearity, however, $$e(t) = h(t) * f\{s(t)\}$$

$$f(s) \approx \sum_{m=1}^{M} a_m s^m \quad (M\text{-th order Taylor series})$$

Where the non-linearity has significant even-numbered Taylor coefficients ($a_m$, m even) the echo is non-zero:

$$e(t) = h(t) * f\{s(t)\} = h(t) * \sum_{m=1}^{M} a_m[1-(-1)^m]s_0^m(t) = h(t) * \sum_{\substack{m=2 \\ m\,even}}^{M} 2a_m s_0^m(t)$$

Typically, the single transmit pulse $s_0(t)$ is amplitude modulated:

$$s_0(t)=p(t)\cos(\omega_0 t-\phi_0).$$

The negated $s_0$ corresponds to a phase shift of $\pi$, which is why this technique is often referred to in the literature as "phase-inversion":

$$s_1(t)=s_0(t)=p(t)\cos(\omega_0 t-\phi_0)$$

$$s_2(t)=p(t)\cos(\omega_0 t-\phi_0-\pi)$$

According to a second embodiment of the invention, more than two phase-related pulses are transmitted into the body.

This leads to an improvement over the prior art phase inversion imaging method, which can be shown as follows:

Generalize the last equation by:

$$s_n(t) = p(t) \text{Re} \cos(\omega_0 t - \phi_0 - \phi_n)$$

and define an extended train of pulses as follows:

$$s(t) = \sum_{n=1}^{N} s_n(t - (n-1)T_{PRF})$$

as well as a new receive signal processing:

$$e(t) = \sum_{n=1}^{N} e_n(t - (N-n)T_{PRF})$$

$$= p(t) * h(t) \sum_{m=1}^{M} a_m \sum_{n=1}^{N} \cos^m(\omega_0 t - \varphi_0 - \varphi_n)$$

$$= p(t) * h(t) \sum_{m=1}^{M} \frac{a_m}{2^m} \sum_{n=1}^{N} b_m(t)$$

$$b_m(t) = 2^m \sum_{n=1}^{N} \cos^m(\omega_0 t - \varphi_0 - \varphi_n)$$

$$= \sum_{n=1}^{N} [e^{j(\omega_0 t - \varphi_0)} e^{-j\varphi_n} + e^{-j(\omega_0 t - \varphi_0)} e^{+j\varphi_n}]^m$$

One can then analyze the Taylor addends:

$$b_m(t) = \begin{cases} \binom{m}{m/2} + \sum_{k=1}^{m/2} \binom{m}{m/2-k} 4\cos[2k(\omega_0 t - \varphi_0)] \sum_{n=1}^{N} \cos 2k\varphi_n & m \text{ even} \\ \sum_{k=1}^{(m+1)/2} \binom{m}{(m+1)/2-k} 4\cos[(2k-1)(\omega_0 t - \varphi_0)] \sum_{n=1}^{N} \cos(2k-1)\varphi_n & m \text{ odd.} \end{cases}$$

Equidistant phases

In case of an equidistant choice of $$\varphi_n : \varphi_n = \frac{2\pi(n-1)}{N},$$

the square addend is suppressed. Consequently, the phase inversion imaging is not improved.

Three Pulses with non equidistant phases

Since the linear Taylor addend becomes zero only in the case of equidistant phases, according to a second embodiment of the invention, a weighted summation is introduced:

$$e(t) = \sum_{n=1}^{N} \alpha_n e_n(t - (N-n)T_{PRF})$$

This can be shown to lead to:

$$b_m(t) = \begin{cases} \binom{m}{m/2} + \sum_{k=1}^{m/2} \binom{m}{m/2-k} 2\text{Re}\left\{ e^{j2k(\omega_0 t - \varphi_0)} \sum_{n=1}^{N} \alpha_n e^{-j2k\varphi_n} \right\} & m \text{ even} \\ \sum_{k=1}^{(m+1)/2} \binom{m}{(m+1)/2-k} 2\text{Re}\left\{ e^{j(2k-1)(\omega_0 t - \varphi_0)} \sum_{n=1}^{N} \alpha_n e^{-j(2k-1)\varphi_n} \right\} & m \text{ odd.} \end{cases}$$

The basic condition that $b_1(t)=0$ leads to $$\sum_{n=1}^{N} \alpha_n w_n = 0$$

Assuming a centered and symmetric phase distribution ($\phi_1=0$ and $\phi_3=-\phi_2$) and a normalized weighting ($\alpha_1=1$):

$$\left. \begin{array}{c} \alpha_1 + (\alpha_2 + \alpha_3)\cos\varphi_2 = 0 \\ (\alpha_2 - \alpha_3)\sin\varphi_2 = 0 \end{array} \right\} \Rightarrow \alpha_3 = \alpha_2 = -\frac{1}{2\cos\varphi_2}.$$

One can then show that $b_2$ and $b_3$ become:

$$b_2(t) = 2 + 2\frac{1 + \cos\varphi_2 - 2\cos^2\varphi_2}{\cos\varphi_2}\cos[2(\omega_0 t - \varphi_0)]$$

$$b_3(t) = 2\frac{1 + 3\cos\varphi_2 - 2\cos^3\varphi_2}{\cos\varphi_2}\cos[3(\omega_0 t - \varphi_0)].$$

Figure 2:
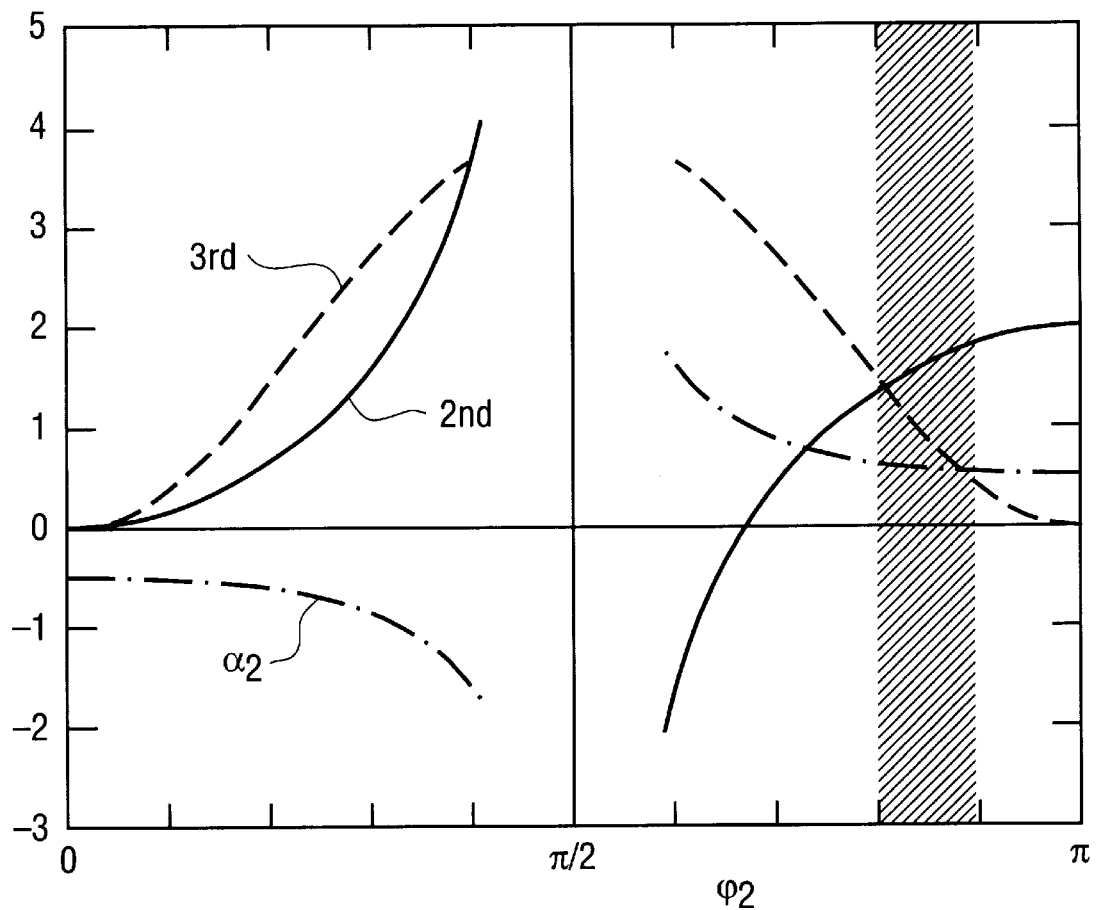
FIG. 2 illustrates the relationship between certain signal parameters and coefficients for a multi-pulse embodiment of the invention.

FIG. 2 illustrates the amplitudes of $b_2(t)$ (solid curves) and $b_3(t)$ (dashed curves) and the weighting factor $\alpha_2$ (dash-dotted curves) as a function of $\phi_2$. The second harmonic is $0.5 \cdot h(t) * a_2 b_2(t)$ and the third harmonic is $0.25 \cdot h(t) * a_3 b_3(t)$. As can be seen, the range from $0.8\pi$ to $0.9\pi$ provides good weighting factors for second and third harmonics.

Five pulses with equidistant phases but separate signal processing

The case $\phi_2=0.8\pi$ is of special interest. In this case $\phi_1$, $\phi_2$, and $\phi_3$ can be seen as a subset (1,3,4) of five phases $\phi_n=2(n-1)\pi/5$. By defining:

$$e^{[i]}(t) = \sum_{n=1}^{N} a_n^{[i]} e_n(t - (N-n)T_{PRF})$$

with the following specifications of of $\alpha_n^{[i]}$ ($\alpha_0 = 1/(2 \cos 0.8\pi)$)

| [i] | $\alpha_1$ | $\alpha_2$ | $\alpha_3$ | $\alpha_4$ | $\alpha_5$ |
|-----|------------|------------|------------|------------|------------|
| 1 | 1 | 0 | $\alpha_0$ | $\alpha_0$ | 0 |
| 2 | 0 | 1 | 0 | $\alpha_0$ | $\alpha_0$ |
| 3 | $\alpha_0$ | 0 | 1 | 0 | $\alpha_0$ |
| 4 | $\alpha_0$ | $\alpha_0$ | 0 | 1 | 0 |
| 5 | 0 | $\alpha_0$ | $\alpha_0$ | 0 | 1 |

This provides five independent measurements with enhanced second and third harmonics. Of course, coherent summation leads to zero. Incoherent summation, however (which is a summation of the demodulated echo signals $e^{[i]}$), does provide a harmonic image with an improved signal-to-noise ratio (SNR).

Phase inversion based on a two-pulse sequence thus allows imaging of even-order harmonics. Due the limited bandwidth of the transducer and the frequency dependent attenuation of tissue only the second-harmonic will appear. As is shown above, a pulse sequence according to the second embodiment of the invention, comprising three pulses with non-equidistant phases, will not cancel out the third harmonic and will, therefore, provide signal enhancement.

Moreover, a sequence of five equidistant (in phase) pulses offers further signal enhancement, since the five pulses can be divided in various subsets of three non-equidistant pulses. Each of these subsets can be considered a three-pulse sequence as discussed above. Incoherent summation of the signals derived from each of these subsets will then lead to further signal enhancement, not only in terms of bandwidth ($2^{nd}$ and $3^{rd}$ harmonics) but also in terms of an improved SNR.

We claim:

1. A method for generating and displaying an image of an interrogation region of a patient's body comprising the following steps:

scanning the interrogation region with an ultrasonic probe by transmitting into the interrogation region with a pulse repetition frequency PRF a sequence of more than two ultrasonic pulses, each pulse having a phase that differs by 180 degrees from the phase of the immediately preceding pulse in the sequence;

calculating a Doppler spectrum of return signals from the sequence of transmitted pulses;

isolating in the Doppler spectrum components of the return signals corresponding to returns from portions of the interrogation region having non-linear response characteristics to the sequence of transmitted pulses; and displaying the scanned interrogation region based on the isolated components of the return signals.

2. A method for generating and displaying an image of an interrogation region of a patient's body comprising the following steps:

scanning the interrogation region with an ultrasonic probe by transmitting into the interrogation region with a pulse repetition frequency PRF a sequence of more than two ultrasonic pulses having non-equidistant relative phase characteristics; and combining return signals from the sequence of pulses and thereby isolating components of the return signals corresponding to returns from portions of the interrogation region having non-linear response characteristics to the sequence of transmitted pulses; and displaying the scanned interrogation region as a predetermined representation of the combined return signals.

3. A method as in claim 1, in which the step of isolating components of the return signals corresponding to returns from portions of the interrogation region having non-linear response includes the following sub-step:

isolating return signals from portions of the interrogation region corresponding to stationary non-linear structures in the interrogation region by pass-band filtering of the return signals with a band-pass filter including zero-frequency (DC) in the pass-band.

4. A method as in claim 1, in which the step of isolating components of the return signals corresponding to returns from portions of the interrogation region having non-linear response includes the following sub-step:

isolating return signals from portions of the interrogation region corresponding to moving non-linear structures in the interrogation region by double pass-band filtering of the return signals with two band-pass filters centered on either side of zero-frequency (DC).

5. A method as in claim 1, in which the step of isolating components of the return signals corresponding to returns from portions of the interrogation region having non-linear response includes the following sub-step:

isolating return signals from portions of the interrogation region corresponding to stationary, linear structures in the interrogation region by pass-band filtering of the return signals with a band-pass filter including a frequency of PRF/2 in the pass-band.

6. A method as in claim 1, in which the step of isolating components of the return signals corresponding to returns from portions of the interrogation region having non-linear response includes the following sub-step:

isolating return signals from portions of the interrogation region corresponding to moving, linear structures in the interrogation region by double pass-band filtering of the return signals with two band-pass filters centered on either side of a frequency of PRF/2.

7. A system for generating and displaying an image of an interrogation region of a patient's body comprising:

an ultrasound probe scanning the interrogation region by transmitting into the interrogation region with a pulse repetition frequency PRF a sequence of more than two ultrasonic pulses, each pulse having a phase that differs by 180 degrees from the phase of the immediately preceding pulse in the sequence;

processing means including:

a Doppler sub-system for calculating a Doppler spectrum of return signals from the sequence of transmitted pulses;

a filter sub-system isolating in the Doppler spectrum components of the return signals corresponding to returns from portions of the interrogation region having non-linear response characteristics to the sequence of transmitted pulses; and display means for displaying the scanned interrogation region based on the isolated components of the return signals.

8. A system as defined in claim 7, in which the filter sub-system includes a band-pass filter having zero-frequency (DC) in the pass-band, thereby isolating return signals from portions of the interrogation region corresponding to stationary non-linear structures in the interrogation.

9. A system as defined in claim 7, in which the filter sub-system includes two band-pass filters centered on either side of zero-frequency (DC), thereby isolating return signals from portions of the interrogation region corresponding to moving non-linear structures.

10. A system as defined in claim 7, in which the filter sub-system includes a band-pass filter having a frequency of PRF/2 in the pass-band, thereby isolating return signals from portions of the interrogation region corresponding to stationary, linear structures.

11. A system as defined in claim 7, in which the filter sub-system includes two band-pass filters centered on either side of a frequency of PRF/2, thereby isolating return signals from portions of the interrogation region corresponding to moving, linear structures.

12. A method as in claim 2, in which:
   there are three ultrasonic pulses in the sequence, namely, a first, a second, and a third ultrasonic pulse;
   the first ultrasonic pulse is a base pulse with a relative phase $\phi_1$ equal to zero;
   the second and third pulses have relative phases $\phi_2$ and $\phi_3$, respectively, where $\phi_2 = -\phi_3$ and the difference between $\phi_1$ and $\phi_2$ is different from the difference between $\phi_2$ and $\phi_3$.

13. A method as in claim 2, in which the step of combining return signals from the sequence of pulses comprises summing the return signals.

14. A method for generating and displaying an image of an interrogation region of a patient's body comprising the following steps:
   scanning the interrogation region with an ultrasonic probe by transmitting into the interrogation region a sequence of five ultrasonic pulses having an equidistant mutual phase separation of $2\pi/5$; and
   forming a combined return signal by incoherently summing return signals from the sequence of five pulses, and thereby isolating components of the return signals corresponding to returns from portions of the interrogation region having non-linear response characteristics to the sequence of transmitted pulses; and
   displaying a visual representation of the combined return signal.

15. A method as in claim 14, in which the step of incoherently summing the return signals comprises forming a weighted sum of the return signals.

16. A method as in claim 14, further including the following steps:
   selecting three-pulse return signal subsets of the return signals from the five ultrasonic pulses having mutually non-equidistant phase separation; and
   forming the combined return signal by incoherently summing the return signals from the three-pulse return signal subsets.

* * * * *